US00PP31240P2

(12) United States Plant Patent
Ruigrok

(10) Patent No.: US PP31,240 P2
(45) Date of Patent: Dec. 17, 2019

(54) ***DAHLIA* PLANT NAMED 'BKDAMAGYL'**

(50) Latin Name: *Dahlia hybrida*
Varietal Denomination: BKDAMAGYL

(71) Applicant: Sanne Helena Ruigrok, Hillegom (NL)

(72) Inventor: Sanne Helena Ruigrok, Hillegom (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 15/999,927

(22) Filed: Aug. 31, 2018

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
See application file for complete search history.

*Primary Examiner* — Anne Marie Grunberg
(74) *Attorney, Agent, or Firm* — C. A. Whealy

(57) ABSTRACT

A new and distinct cultivar of *Dahlia* plant named 'BKDAMAGYL', characterized by its upright plant habit; moderate basal branching habit; dense and bushy growth habit; large dark green-colored leaves; and large decorative type inflorescences with bright yellow-colored ray florets.

2 Drawing Sheets

Botanical designation: *Dahlia hybrida.*
Cultivar denomination: 'BKDAMAGYL'.

BACKGROUND OF THE INVENTION

The present invention relates to a new and distinct cultivar of *Dahlia* plant, botanically known as *Dahlia hybrida* and hereinafter referred to by the name 'BKDAMAGYL'.

The new *Dahlia* plant is a product of a planned breeding program conducted by the Inventor in Hillegom, The Netherlands. The objective of the breeding program is to create new large container *Dahlia* plants with large and attractive decorative type inflorescences.

The new *Dahlia* plant originated from a cross-pollination in September, 2013 in Hillegom, The Netherlands of a proprietary selection of *Dahlia hybrida* identified as code number FET.S12.013.023, not patented, as the female, or seed, parent with a proprietary selection of *Dahlia hybrida* identified as code number FET.S12.011.005, not patented, as the male, or pollen, parent. The new *Dahlia* plant was discovered and selected by the Inventor as a single flowering plant from within the progeny of the stated cross-pollination in a controlled greenhouse environment in Hillegom, The Netherlands in October, 2015.

Asexual reproduction of the new *Dahlia* plant by vegetative terminal cuttings in a controlled greenhouse environment in Maasdijk, The Netherlands since February, 2016 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMAGYL'. These characteristics in combination distinguish 'BKDAMAGYL' as a new and distinct *Dahlia* plant:

1. Upright plant habit.
2. Moderate basal branching habit; dense and bushy growth habit.
3. Large dark green-colored leaves.
4. Large decorative type inflorescences with bright yellow-colored ray florets.

Plants of the new *Dahlia* differ primarily from plants of the female parent selection in the following characteristics:

1. Plants of the new *Dahlia* are taller than plants of the female parent selection.
2. Inflorescences of plants of the new *Dahlia* are larger than inflorescences of plants of the female parent selection.

Plants of the new *Dahlia* differ primarily from plants of the male parent selection in the following characteristics:

1. Plants of the new *Dahlia* are shorter than plants of the male parent selection.
2. Ray florets of plants of the new *Dahlia* are bright yellow in color whereas ray floret of plants of the male parent selection are yellow orange in color.

Plants of the new *Dahlia* can be compared to plants of *Dahlia hybrida* 'XXL Durango', not patented. In side-by-side comparisons, plants of the new *Dahlia* differ from plants of 'XXL Durango' in the following characteristics:

1. Inflorescences of plants of the new *Dahlia* are decorative in form whereas inflorescences of plants of 'XXL Durango' are "waterlily" in form.
2. Ray florets of plants of the new *Dahlia* are bright yellow in color whereas ray florets of plants of 'XXL Durango' are paler yellow in color.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'BKDAMAGYL' grown in a container.

The photograph on the second sheet is a close-up view of a typical inflorescence of 'BKDAMAGYL'.

DETAILED BOTANICAL DESCRIPTION

The aforementioned photographs and the following observations and measurements describe plants grown during the spring in 19-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were 14 weeks old when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDAMAGYL'.

Parentage:

*Female, or seed, parent*.—Proprietary selection of *Dahlia hybrida* identified as code number FET.S12.013.023, not patented.

*Male, or pollen, parent*.—Proprietary selection of *Dahlia hybrida* identified as code number FET.S12.011.005, not patented.

Propagation:

*Type*.—By vegetative terminal cuttings.

*Time to initiate roots, summer*.—About 16 days at temperatures ranging from 18° C. to 21° C.

*Time to initiate roots, winter*.—About 19 days at temperatures ranging from 19° C. to 21° C.

*Time to produce a rooted young plant, summer*.—About 23 days at temperatures ranging from 18° C. to 21° C.

*Time to produce a rooted young plant, winter*.—About 25 days at temperatures ranging from 19° C. to 21° C.

*Root description*.—Medium in thickness, fibrous; typically white in color, actual color of the roots is dependent on substrate composition, water quality, fertilizers, substrate temperature and physiological age of roots; tuber development has not been observed on plants of the new *Dahlia*.

*Rooting habit*.—Moderately freely branching; medium density.

Plant description:

*Plant and growth habit*.—Upright and mounding plant form; overall plant shape, globular; moderate basal branching habit with about four primary branches each with about two secondary branches developing per plant; inflorescences held above and beyond the foliar plane on strong peduncles; bushy and dense growth habit; pinching is not required but will improve branching habit; moderately vigorous growth habit; moderate growth rate.

*Plant height, soil level to top of foliar plane*.—About 33.4 cm.

*Plant height, soil level to top of floral plane*.—About 40.8 cm.

*Plant diameter or spread*.—About 50.3 cm.

*Lateral branches*.—Length: About 18.4 cm. Diameter: About 8 mm. Internode length: About 5.5 cm. Aspect: Primary branches are about 40° from vertical; secondary branches, about 30° from primary branch axis. Strength: Moderately strong. Texture and luster: Smooth, glabrous; glossy. Color, developing: Close to 144A. Color, developed: Close to between 144A and 146C.

Leaf & leaflet description:

*Arrangement*.—Leaves opposite and compound with three or five leaflets.

*Length, compound leaves*.—About 15.8 cm.

*Length, terminal leaflets*.—About 14.1 cm.

*Length, lateral leaflets*.—About 10.1 cm.

*Width, compound leaves*.—About 18 cm.

*Width, terminal leaflets*.—About 6.7 cm.

*Width, lateral leaflets*.—About 4.4 cm.

*Shape, compound leaves in overall outline*.—Broadly ovate.

*Shape, terminal leaflets*.—Obovate.

*Shape, lateral leaflets*.—Elliptic to obovate.

*Apex, leaflets*.—Apiculate.

*Base, terminal leaflets*.—Long and narrowly attenuate.

*Base, lateral leaflets*.—Attenuate to long attenuate.

*Margin, leaflets*.—Coarsely serrate.

*Venation pattern, leaflets*.—Pinnate.

*Texture and luster, upper surface, leaflets*.—Smooth, glabrous; slightly velvety; slightly glossy.

*Texture and luster, lower surface, leaflets*.—Mostly smooth and glabrous; sparsely pubescent along venation; matte.

*Color*.—Developing leaflets, upper surface: Close to between NN137A and 147A. Developing leaflets, lower surface: Close to between 146B and 147B. Fully expanded leaflets, upper surface: Close to between 147A and N189A; venation, close to 144A. Fully expanded leaflets, lower surface: Close to 191A; venation, close to 146B.

*Petioles, leaflets*.—Length: About 5.2 cm. Diameter: About 4 mm by 4.5 mm. Strength: Moderately strong. Texture and luster, upper and lower surfaces: Smooth, glabrous; glossy. Color, upper and lower surfaces: Close to 144A.

Inflorescence description:

*Appearance and arrangement*.—Large decorative type inflorescences with ray and disc florets forming acropetally on a receptacle; inflorescences positioned above and beyond the foliar plane on strong peduncles; inflorescences face mostly upright to slightly outwardly; freely flowering habit with about 36 inflorescences developing per plant.

*Fragrance*.—None detected.

*Flowering response and flowering period*.—Plants begin flowering about 84 days after planting; plants flower continuously during the autumn into the winter in The Netherlands.

*Post-production longevity*.—Inflorescences maintain good substance for about ten days on the plant; inflorescences persistent; plants maintain good substance for about three months.

*Inflorescence buds*.—Height: About 1.5 cm. Diameter: About 1.6 cm. Shape: Flattened globular. Texture and luster: Smooth, glabrous; glossy. Color: Close to 154A; fading towards the base to close to 143A.

*Inflorescence size*.—Diameter: About 11.5 cm. Depth (height): About 8.8 cm. Disc diameter: About 2 cm.

*Receptacles*.—Height: About 5 mm. Diameter: About 1 cm. Shape: Dome-shaped. Color: Close to 145C.

*Ray florets*.—Quantity per inflorescence and arrangement: About 120 arranged in about six whorls. Length: About 5.5 cm. Width: About 1.7 cm. Shape: Oblanceolate. Apex: Broadly acute. Base: Cuneate. Margin: Entire. Aspect: Varying from −40° to 40° from horizontal. Texture and luster, upper and lower surfaces: Smooth, glabrous; velvety; matte. Color: When opening, upper surface: Close to between 1A and 2A. When opening, lower surface: Close to 1A. Fully opened, upper surface: Close to 1B; fading darker towards the base to close to 1A; venation, similar to lamina colors; color does not change with development. Fully opened, lower surface: Close to 1B to 1C; fading darker towards the base to close to 1B; venation, similar to lamina colors; color does not change with development.

*Disc florets*.—Quantity per inflorescence and arrangement: About 30 massed at the center of the inflorescence in about five spiral whorls. Length: About 1.8 cm. Diameter: About 5.5 mm. Shape: Tubular, elongated; apices, acute. Texture and luster, inner and outer surfaces: Smooth, glabrous; glossy. Color, when opening, inner and outer surfaces: Towards the apex, close to 15A; mid-section, close to 154B; towards the base, close to 145D. Color, fully opened, inner and outer surfaces: Towards the apex, close to 14A; mid-section, close to 154B; towards the base, close to 145D; colors do not change with development.

*Phyllaries*.—Quantity per inflorescence and arrangement: About nine arranged in a single whorl. Length: About 1.3 cm. Width: About 4.5 mm. Shape: Narrowly obovate. Apex: Broadly acute. Base: Cuneate. Margin: Entire. Texture and luster, upper and lower surfaces: Smooth, glabrous; moderately glossy. Color, upper surface: Close to NN137B. Color, lower surface: Close to NN137C.

*Ray floret bracts*.—Quantity per inflorescence and arrangement: One subtending each ray floret. Length: About 1.9 cm. Width: About 5.5 mm. Shape: Oblong. Apex: Broadly acute. Base: Broadly cuneate. Margin: Entire. Texture and luster, upper and lower surfaces: Smooth, glabrous; glossy. Color, upper and lower surfaces: Towards the apex, close to 150B; mid-section, close to N144D; towards the base, close to 143A.

*Peduncles*.—Length, terminal peduncle: About 13 cm. Diameter, terminal peduncle: About 3 mm. Strength: Strong. Texture and luster: Smooth, glabrous; glossy. Color: Close to 144A.

*Reproductive organs*.—Androecium, present on disc florets only: Quantity per floret: About five. Filament length: About 5 mm. Filament color: Close to 150D. Anther shape: Narrowly oblong. Anther length: About 5 mm. Anther diameter: About 0.5 mm. Anther color: Close to between 12A and 13A. Pollen amount: Moderate. Pollen color: Close to 23A. Gynoecium, present on ray and disc florets: Quantity per floret: One. Pistil length: About 1.4 cm. Style length: About 3 mm. Style color: Close to 150C to 150D. Stigma diameter: About 5.5 mm. Stigma shape: Cleft. Stigma color: Close to 14A. Ovary color: Close to 145C. Seeds and fruits: To date, seed and fruit development have not been observed on plants of the new *Dahlia*.

Disease & pest resistance: To date, plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAMAGYL' as illustrated and described.

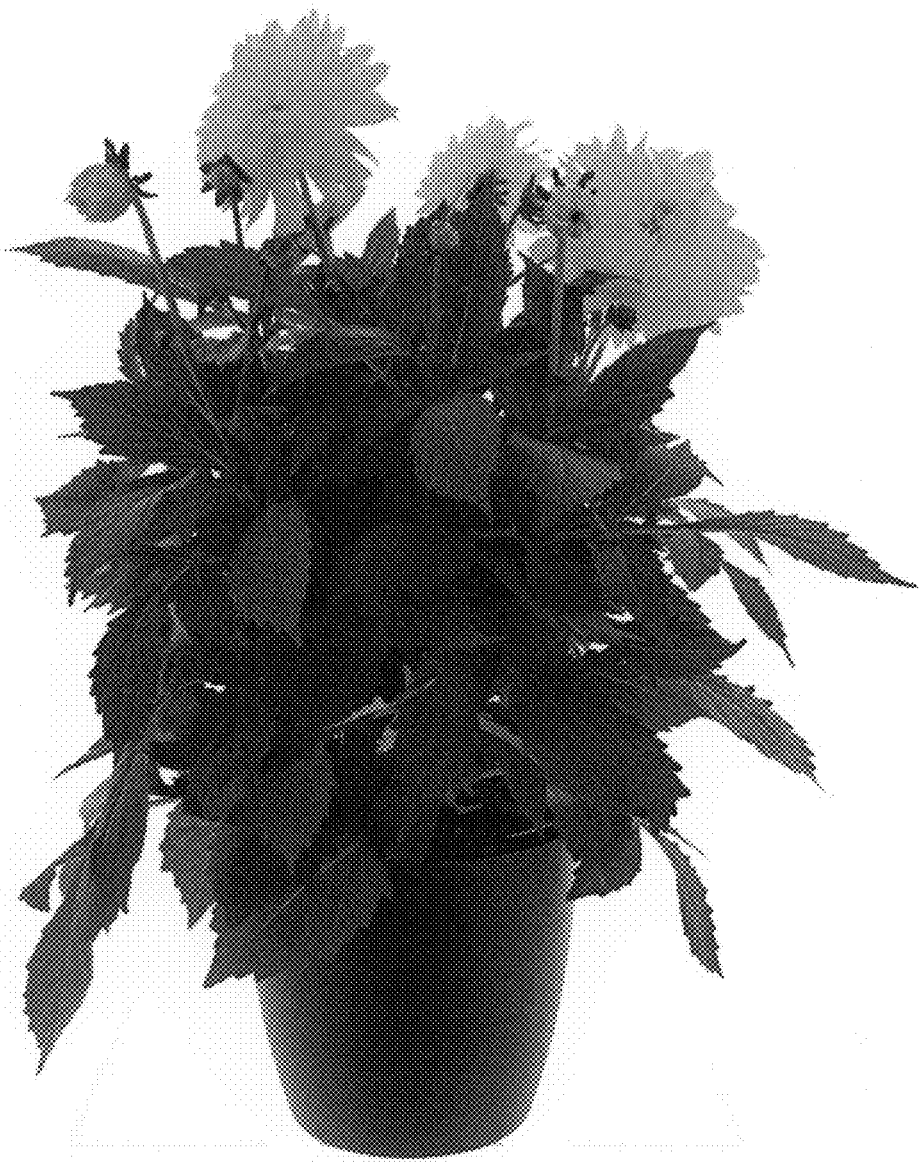

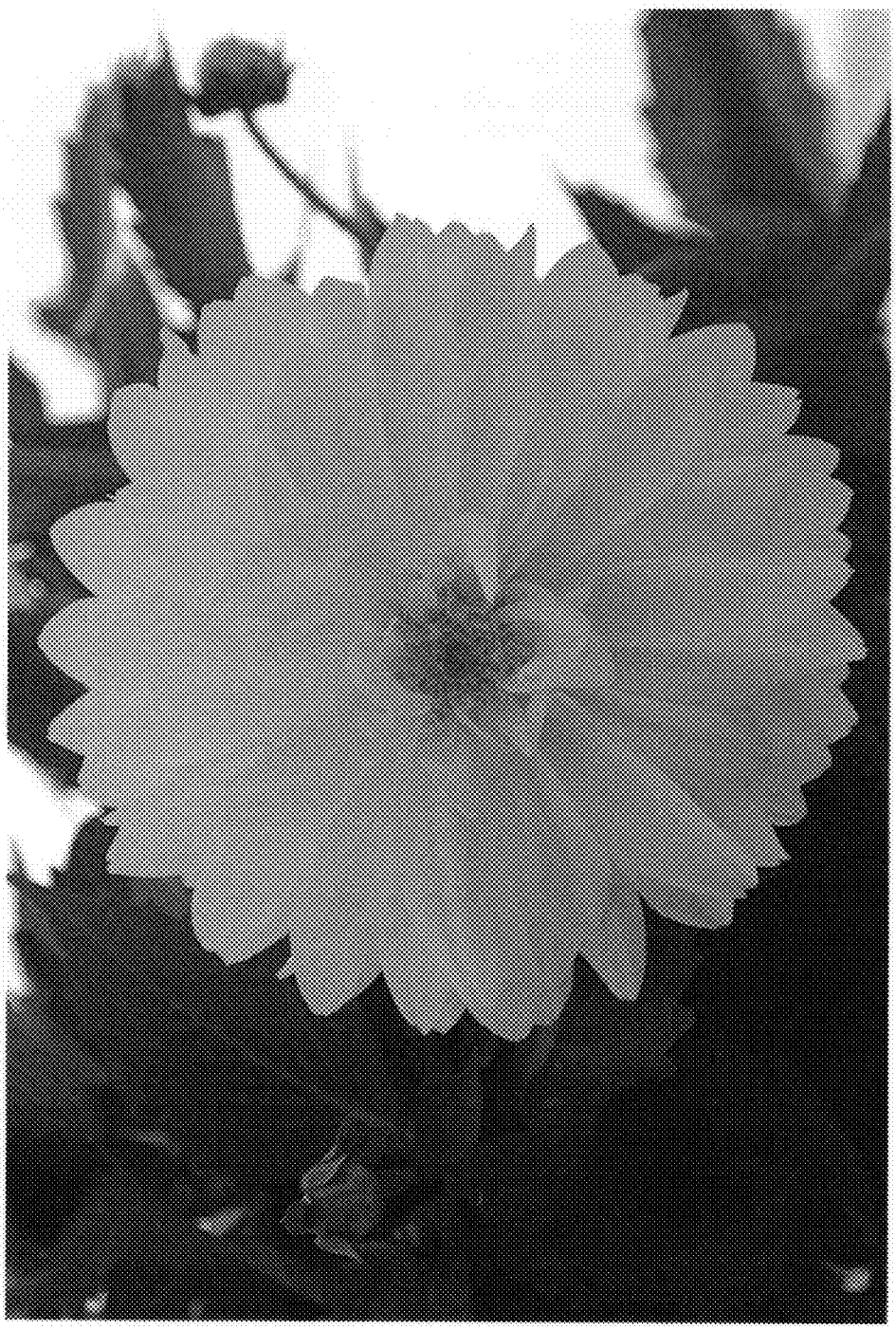

* * * * *